United States Patent
Song (10) Patent No.: US 9,194,807 B2
(45) Date of Patent: Nov. 24, 2015

(54) MULTI-LAYERED DEVICES FOR ANALYTE DETECTION

(71) Applicant: Kimberly-Clark Worldwide, Inc., Neenah, WI (US)

(72) Inventor: Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/727,911

(22) Filed: Jun. 2, 2015

(65) Prior Publication Data
US 2015/0260658 A1 Sep. 17, 2015

Related U.S. Application Data

(62) Division of application No. 11/956,420, filed on Dec. 14, 2007, now Pat. No. 9,103,796.

(51) Int. Cl.
| | |
|---|---|
| *G01N 21/78* | (2006.01) |
| *C12Q 1/44* | (2006.01) |
| *G01N 33/84* | (2006.01) |
| *G01N 21/75* | (2006.01) |
| *G01N 21/77* | (2006.01) |

(52) U.S. Cl.
CPC ...... *G01N 21/78* (2013.01); *C12Q 1/44* (2013.01); *G01N 33/84* (2013.01); *G01N 2021/752* (2013.01); *G01N 2021/7759* (2013.01)

(58) Field of Classification Search
CPC .......... G01N 21/78; G01N 2021/7759; G01N 33/525
USPC .................................................. 435/7.7, 7.92
See application file for complete search history.

(56) References Cited

U.S. PATENT DOCUMENTS

| | | |
|---|---|---|
| 3,634,198 A | 1/1972 | Truhan |
| 3,712,853 A | 1/1973 | Rittersdorf et al. |
| 4,278,763 A | 7/1981 | Berger et al. |
| 4,299,917 A | 11/1981 | Berger et al. |
| 4,366,241 A | 12/1982 | Tom et al. |
| 4,472,498 A | 9/1984 | Masuda et al. |
| 4,631,255 A | 12/1986 | Takino et al. |
| 4,637,979 A | 1/1987 | Skjold et al. |
| 4,657,855 A | 4/1987 | Corey et al. |
| 4,704,116 A | 11/1987 | Enloe |
| 4,806,423 A | 2/1989 | Hugl et al. |
| 4,814,271 A | 3/1989 | Hugl et al. |
| 4,868,131 A | 9/1989 | Hiratsuka |
| 4,975,366 A | 12/1990 | Sudo et al. |

(Continued)

FOREIGN PATENT DOCUMENTS

| | | |
|---|---|---|
| EP | 160240 | 11/1985 |
| EP | 0759555 | 2/1997 |
| WO | WO 9516425 | 6/1995 |

*Primary Examiner* — Shogo Sasaki
(74) *Attorney, Agent, or Firm* — Dority & Manning, P.A.

(57) ABSTRACT

A multi-layered device for detecting the presence or absence of an analyte within a test sample is described. The device includes a sensing layer and a control layer. The sensing layer is configured to support a reaction so as to exhibit a signal indicative of the presence or absence of the analyte in the test sample. The control layer is in fluid communication with and vertically adjacent to the sensing layer and includes a reagent capable of inhibiting the reaction and/or other unwanted side reactions at the sensing layer after a certain period of time by diffusive movement of the reagent from the control layer to the sensing layer.

17 Claims, 3 Drawing Sheets

(56) References Cited

U.S. PATENT DOCUMENTS

| | | |
|---|---|---|
| 5,192,606 A | 3/1993 | Proxmire et al. |
| 5,399,219 A | 3/1995 | Roessler et al. |
| 5,464,739 A | 11/1995 | Johnson et al. |
| 5,468,236 A | 11/1995 | Everhart et al. |
| 5,486,166 A | 1/1996 | Bishop et al. |
| 5,490,846 A | 2/1996 | Ellis et al. |
| 5,512,450 A | 4/1996 | Johnson et al. |
| 5,540,796 A | 7/1996 | Fries |
| 5,595,618 A | 1/1997 | Fries |
| 5,663,044 A | 9/1997 | Noffsinger et al. |
| 5,702,377 A | 12/1997 | Collier, IV et al. |
| 5,750,359 A | 5/1998 | Huh et al. |
| 5,762,871 A | 6/1998 | Neyer |
| 5,931,826 A | 8/1999 | Faulks et al. |
| 6,048,735 A | 4/2000 | Hessel et al. |
| 6,060,638 A | 5/2000 | Paul et al. |
| 6,150,002 A | 11/2000 | Varona |
| 6,399,853 B1 | 6/2002 | Roe et al. |
| 6,663,611 B2 | 12/2003 | Blaney et al. |
| 6,750,006 B2 | 6/2004 | Powers et al. |
| 2004/0102750 A1 | 5/2004 | Jameson |
| 2005/0054255 A1 | 3/2005 | Morman et al. |
| 2005/0059941 A1 | 3/2005 | Baldwin et al. |
| 2007/0048182 A1 | 3/2007 | Song et al. |
| 2008/0103414 A1 | 5/2008 | Song |
| 2008/0145949 A1 | 6/2008 | Song et al. |
| 2008/0269707 A1 | 10/2008 | Song |

MULTI-LAYERED DEVICES FOR ANALYTE DETECTION

BACKGROUND

Multiple tests have been developed for detecting components in urine. Such tests can provide information about overall health as well as provide an indication of a health problem. When timely administered, such tests can also be able to provide an early indication of a health problem, which can be very advantageous for effective treatment. By way of examples, urine testing can be used to detect urinary tract infections, diabetes (including diabetic ketoacidosis), parasites, dehydration, dietary defects, cancer, high blood pressure, kidney disease, asthma, severe emphysema, alcoholism, systemic lupus erythematosus (SLE), glomerulonephritis, and leukemia.

Such tests can be performed by having a patient voluntarily collect and provide a sample. However, patient collected urine samples may not be readily available with certain test subjects such as children, elderly adults, and injured or non-ambulatory patients. Additionally, it can be preferable to collect and test urine samples from these subjects at certain times or conditions where the patient is not necessarily in the presence of medical or otherwise specially trained personnel. Frequently, such subjects can be provided with a diaper or other absorbent article to collect urine and provide for disposal in a hygienic manner. Of course, these articles must be periodically checked to determine whether urine and other bodily waste has been collected. In addition, current test methods generally require a controlled reading window. However, it is not always feasible to carefully monitor testing, particularly in consumer-based applications.

Specific developments have been provided for collecting and detecting urine samples using a diaper and/or an absorbent article. Nonetheless, tests can still display inaccurate results if left in air or other oxidizing environments for too great a period of time. For instance, certain compounds can undergo an oxidation reaction if left in air or other oxidizing environment for too great a period of time. The resulting oxidized compounds can possess a certain color that indicates a "false positive" or at the very least, adversely affect the ability to determine the presence or absence of the analytes. Additionally, multiple urine insults can affect the accuracy of test results.

Thus, a need exists for testing devices that do not need careful monitoring to obtain accurate results. An absorbent article that incorporates such a device would be particularly beneficial. Additionally, an absorbent article that can also provide, in certain embodiments, an effective urine test for detecting and reporting a urinary tract infection would also be particularly beneficial.

SUMMARY

In accordance with one embodiment of the present disclosure, a multi-layered device for detecting the presence or absence of an analyte within a test sample is described. The device includes a sensing layer and a control layer. The sensing layer is configured to support a reaction so as to exhibit a signal indicative of the presence or absence of the analyte in the test sample. The control layer is in fluid communication with and vertically adjacent to the sensing layer and includes a reagent capable of inhibiting the reaction at the sensing layer by diffusive movement of the reagent from the control layer to the sensing layer. In another embodiment of the present disclosure, a multi-layered device for detecting the presence or absence of an enzyme within a test sample is described. The sensing layer includes a substrate capable of being modified in the presence of the enzyme to release a product utilized to indicate the presence or absence of the enzyme in the test sample. The control layer is in fluid communication with and vertically adjacent to the sensing layer and includes a control reagent capable of inhibiting the reaction and/or other unwanted side reactions at the sensing layer by diffusive movement of the control reagent from the control layer to the sensing layer.

In yet another embodiment of the present disclosure, a multi-layered device for detecting the presence or absence of a nitrite within a test sample is described. The sensing layer includes an aromatic primary amine and a detection reagent. The aromatic primary amine is capable of reacting with a nitrite to form a diazonium ion and the detection reagent is capable of reacting with the diazonium ion to form an indicator, the indicator exhibiting a color indicative of the presence or absence of the nitrite in the test sample. The control layer is in fluid communication with and vertically adjacent to the sensing layer and includes a control reagent capable of inhibiting the reaction and/or other unwanted side reactions at the sensing layer by diffusive movement of the control reagent from the control layer to the sensing layer.

In still another embodiment of the present disclosure, an absorbent article for receiving a bodily fluid suspected of containing an analyte is described. The absorbent article includes a substantially liquid impermeable layer, a liquid permeable layer, and an absorbent core positioned between the substantially liquid impermeable layer and the liquid permeable layer. A multi-layered device in accordance with the present disclosure is integrated into the article and positioned such that the device is in fluid communication with the bodily fluid when provided by a wearer of the article.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figure in which.

Repeat use of reference characters in the present specification and drawings is intended to represent same or analogous features or elements of the disclosure.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 4,366,241 to Tom et al.

As used herein, the term "test sample" generally refers to any material suspected of containing analytes. The test sample can be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples can be used such as water, food products, and so forth, for the performance of environmental or food production assays. In addition, a solid material suspected of containing analytes can be used as the test sample. The test sample can be used directly as obtained from the biological source or following a pretreatment to modify the character of the sample. For example, such pretreatment can include preparing plasma from blood, diluting viscous fluids, and so forth. Methods of pretreatment can also involve filtration, precipitation, dilution, distillation, mixing, concentration, inactivation of interfering components, the addition of reagents, lysing, etc. Moreover, it can also be beneficial to modify a solid test sample to form a liquid medium or to release the analytes.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to a multi-layered device for detecting the presence or absence of one or more analytes in a test sample. Very generally, the device includes one or more sensing layers configured to support a reaction so as to exhibit a signal indicative of the presence or absence of the analyte in the test sample. In addition, the device includes one or more control layers in fluid communication with and vertically adjacent to the sensing layer. The control layer(s) includes one or more reagents capable of inhibiting the reaction at the sensing layer by diffusive movement of the reagent from the control layer(s) to the sensing layer(s).

Various embodiments for accomplishing the detection of an analyte using a multi-layered device are described herein. For instance, referring to FIG. 1, a multi-layered device 10 in accordance with one embodiment of the present disclosure is illustrated. As shown, the device includes a sensing layer 12 and a control layer 14 in a vertically adjacent relationship. The device optionally includes a support 16.

Figure 1:
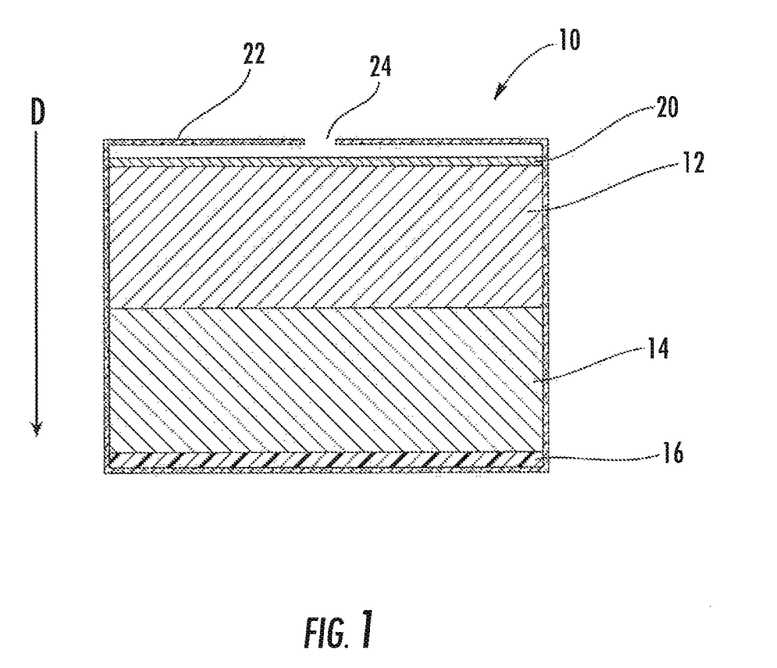
FIG. 1 is a perspective view of one embodiment of a device that can be used in the present disclosure.

The application of a sufficient volume of a test sample to the device 10 can cause a signal to form within the sensing layer 12 indicating whether or not the analyte of interest is present. The device also includes a control layer 14 in fluid communication with the sensing layer 12. The test sample can move from the sensing layer 12 to the control layer 14 and thereby cause diffusive movement of a control reagent back to the sensing layer 12. The control reagent is capable of inhibiting the reaction and/or other unwanted side reactions at the sensing layer after a certain period of time. In this manner, the testing devices of the present disclosure do not need careful monitoring to obtain accurate results.

As described above, certain compounds can undergo an unwanted oxidation reaction if left in air or other oxidizing environment for too great a period of time. Multiple urine insults can also affect the accuracy of test results. However, with the control reagent diffusively moving to the sensing layer and inhibiting the unwanted reaction at the sensing layer, as described in the present disclosure, such problems can be greatly minimized.

For instance, in certain embodiments, the device 10 can include control reagents that are capable of inhibiting an enzyme-catalyzed substrate reaction. The control reagents can include enzyme inhibitors (competitive (binds to enzyme), uncompetitive (binds to enzyme-substrate complex), or noncompetitive (binds to enzyme and/or enzyme-substrate complex)), and the like.

In still other embodiments, control reagents can be selectively controlled as desired to impact reaction time. Suitable control reagents to speed an enzyme reaction can include for hydrolytic esterases can include, for instance, pyridine, imidazole and their derivatives, metal complexes, and alcohols. Particularly useful alcohols are linear alcohols having 1 to 15 carbon atoms, such as decanol, undecanol and dodecanol. Other examples of suitable control reagents are described in U.S. Pat. No. 4,657,855 to Corey. et al. and U.S. Pat. No. 4,299,917 to Berger, et al., which are incorporated herein in their entirety by reference thereto for all purposes.

The pH can also be selectively controlled to enhance enzyme activity and to inhibit unwanted side reactions. For instance, many ester substrates are unstable in highly basic or highly acidic conditions due to their tendency to hydrolyze. Thus, the pH is typically maintained at a relatively neutral level, such as from about 6 to about 9, and in some embodiments, about 7. However, the control reagents of the present disclosure can alter the pH so as to alter the speed of the reaction. Some biologically compatible buffers that can be utilized as control reagents in the present disclosure to maintain the desired pH include borate buffers, phosphate-buffered saline (PBS), 2-(N-morpholino) ethane sulfonic acid ("MES"), tris-hydroxymethylaminomethane ("Tris"), citrate buffers, and the like.

Similarly, the pH can be adjusted with control reagent buffers to inhibit a nitrite reaction, such as described above. For instance, the pH is typically maintained at a level of less than about 6, and in some embodiments, from about 1 to about 4. However, the control reagents of the present disclosure can be utilized to alter the pH so as to alter the speed of the reaction. Some examples of suitable control reagents that can be used in the present disclosure include, but are not limited to, mineral acids, sulfonic acids (e.g., 2-[N-morpholino] ethane sulfonic acid ("MES"), carboxylic acids, and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid.

In addition, suitable control reagents can include bases and buffer compounds. Examples of suitable bases include sodium bicarbonate, sodium carbonate, sodium borate, sodium hydroxide, potassium hydroxide, or combinations thereof.

As illustrated in FIG. 1, the control layer 14 is in fluid communication with the sensing layer 12. The test sample can move from the sensing layer 12 to the control layer 14 and thereby cause diffusive movement of the control reagent(s) back to the sensing layer 12. In this manner, the control reagent is capable of inhibiting the reaction at the sensing layer 12. For example, in some embodiments, the control layer 14 is positioned underneath the sensing layer 12. Due to the separation provided between the sensing layer 12 and control layer 14, the likelihood of any control reagent diffusing into the sensing layer 12 prematurely is thus reduced.

As described above, the multi-layered device of the present disclosure also employs one or more sensing layers for providing an indication of the presence of an analyte. More specifically, such layer(s) typically contain a chemical or biological reagent that interacts with the analyte and/or other reagents to generate a signal (e.g., visual signal). Referring again to FIG. 1, for example, the multi-layered device 10 includes a sensing layer 12 within which a capture reagent is disposed. Typically, the capture reagent is applied in a manner so that it does not substantially diffuse through the matrix of the sensing layer 12 (i.e., non-diffusively immobilized). This enables a user to readily detect the change in color that occurs upon reaction of the capture reagent with other compounds. The capture reagent can, for example, form an ionic and/or covalent bond with functional groups present on the surface of the sensing layer 12 so that it remains immobilized thereon. For instance, particles, such as described below, can facilitate the immobilization of the reagent at the sensing layer 12. Namely, the reagent can be coated onto particles, which are then immobilized on the sensing layer 12 of the device 10. In this manner, the reagent is able to readily contact compounds flowing through the multi-layered device 10.

If desired, one or more of the reagents employed in the assay device can be disposed on particles (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. Although any synthetic particle can be used in the present disclosure, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles can generally vary. In one particular embodiment, for instance, the particles are spherical in shape. However, it should be understood that other shapes are also contemplated by the present disclosure, such as plates, rods, discs, bars, tubes, irregular shapes, etc. In addition, the size of the particles can also vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns. Commercially available examples of suitable particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the sensing layer 12 and control layer 14 can vary based on the nature of the test being performed. In the illustrated embodiment, for example, the sensing layer 12 is vertically adjacent to the control layer 14 and positioned so that the control layer 14 is directly underneath the sensing layer 12. In such embodiments, the sensing layer 12 can contain a material that is non-diffusively immobilized in the manner described above and forms a chemical and/or physical bond with the sensing reagents.

The specific reagents employed in the devices of the present disclosure depend on the analyte of interest. In one particular embodiment, for example, it can be desirable to detect the presence of leukocytes in urine as an early diagnosis of urinary tract infection ("UTI"). Although leukocytes are normally present in the urine, it has been determined that the threshold limit for pathological levels is about $1 \times 10^4$ leukocytes per milliliter of uncentrifuged urine. When leukocytes are present in urine, leukocyte esterase is produced and can be used as a biomarker for the presence of leukocytes.

A variety of reagents can be used for detecting the presence of the leukocyte esterase enzyme. One such reagent is a substrate that is chemically acted upon or "cleaved" by the enzyme of interest to release a product. For example, the substrate can be an ester that is catalytically hydrolyzed in the presence of leukocyte esterase to yield an aromatic compound. The aromatic esters can include, for instance, indoxyl esters having the following general formula:

wherein, R can be substituted or unsubstituted, and can be an alkyl group, an alkyoxy group, a hydroxyalkyl group, an alkylene group, a fatty acid group, and so forth. In addition, the aromatic rings can also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

Lactate esters can also be used, such as described in U.S. Pat. No. 5,464,739 to Johnson, et al. and U.S. Pat. No. 5,663,044 to Noffsinger, et al., which are incorporated herein in their entirety by reference thereto for all purposes. Lactate esters are generally hydrolyzed by the leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750,359 to Huh, et al.; U.S. Pat. No. 4,657,855 to Corey, et al.; and Japanese Publication No. 03210193 to Kawanishi, et al., which are incorporated herein in their entirety by reference thereto for all purposes.

Typically, the substrate is diffusively immobilized on the device 10 prior to application of the urine or other bodily fluid. Regardless, an aromatic compound is released through cleavage of the substrate that is capable of inducing a color change in the presence of certain reagents. The released aromatic compound is a nucleophile in that it contains a group that is electron rich (e.g., amine) and that can form bonds with electron deficient groups. For example, indoxyl esters are hydrolyzed by the leukocyte esterase to form indoxyl. Indoxyl contains an electron-rich, aromatic ring system that is capable of undergoing electrophilic attack by a diazonium ion having the generic formula:

The diazonium ion can be zwitterionic in that the counterion of the diazonium moiety is covalently bound to the ring system. The ring system of the diazonium ion can be substituted or unsubstituted. The ion can be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate, One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

Other suitable diazonium salts are classified by the common names "Fast Red B" and "Fast Blue B." Still other suitable diazonium salts can be described in U.S. Pat. No. 4,637,979 to Skjold, et al.; U.S. Pat. No. 4,806,423 to Hugh, et al.; and U.S. Pat. No. 4,814,271 to Hugl, et al., which are incorporated herein in their entirety by reference thereto for all purposes.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions can react with aromatic compounds to form an aromatic azo compound having the generic formula, R—N=N—R', wherein "R" and "R" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of leukocyte esterase or other enzymes within the test sample. For example, prior to contact with an infected test sample, the diazonium ion can be colorless or it can possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that can be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, can react with indoxyl to form an aromatic azo compound that is red and has the following general structure (can be substituted or unsubstituted):

Normally, the above-described diazonium ion is immobilized within the sensing layer 12 of the device 10. The diazonium ion can be applied directly to the sensing layer 12 or first formed into a solution prior to application. Various solvents can be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution can range from about 0.001 to about 100 milligrams per milliliter of solvent, and in some embodiments, from about 0.1 to about 10 milligrams per milliliter of solvent. The diazonium ion concentration can be selectively controlled to provide the desired level of detection sensitivity.

Typically, the diazonium ion can be applied in a manner so that it does not substantially diffuse through the matrix of the sensing layer 12 (i.e., non-diffusively immobilized). This enables a user to readily detect the change in color that occurs upon reaction of the diazonium ion with a nucleophilic aromatic compound. The diazonium ion can form an ionic and/or covalent bond with functional groups present on the surface of the sensing layer 12 so that it remains immobilized thereon.

An exemplary method for detecting the presence of leukocyte esterase within a test sample using the device 10 of FIG. 1 will now be described in more detail. Initially, urine containing leukocyte esterase is discharged to device 10 and travels in the direction "D". The esterase is able to mix with and begin to initiate the catalytic reaction at the sensing layer 12. The enzyme and substrate react to release an aromatic product that subsequently couples with a diazonium ion to form a colored aromatic azo compound at the sensing layer 12. After the reaction, the sensing layer 12 changes color, which can be indicative of urinary tract infection. The device also includes a control layer 14 in fluid communication with the sensing layer 12. The test sample moves from the sensing layer 12 to the control layer 14 and thereby causes diffusive movement of a control reagent back to the sensing layer 12. The control reagent is capable of inhibiting the reaction at the sensing layer. Affecting the speed of the reaction can allow the sensing layer 12 to be tolerant of multiple urine insults without affecting the signal over an extended period of time.

The presence of nitrites in urine can also indicate a urinary tract infection or even other bacterial infections in the body. A variety of reagents are used to accomplish the detection of nitrites. For example, aromatic primary amines can be employed that have the ability to react with nitrite ions under certain conditions. Aromatic primary amines are amines in which at least one primary amino group is connected to an aromatic ring. Aromatic primary amines can, for instance, have the following formula:

wherein positions 1 through 5 can be unsubstituted or substituted with a moiety, such as alkyl, alkylene, halogen, phenyl, hydroxyl, amino, amide, carboxyl, sulfonic, aromatic amine, aromatic amide, and other moieties. Particularly desired aromatic primary amines are those that are able to readily react with nitrite ions (or nitrous acid). Exemplary aromatic primary amines can include, for instance, aniline; 4-chloroaniline; 4-bromoaniline; 2,4,6-tribromoaniline; 2,4,6-trichloroaniline; α-trifluoro-m-toluidene; ortho-toluidine; m- and p-aminophenol; ortho-tolidine; sulfanilamide, p-aminobenzoic acid; 1-amino-8-hydroxynaphthalene-3, 6-disulphonic acid; aminoacetoanilide; aminophenyl ether, p-arsalinic acid; 4-amino-1-naphthalenecarbonitrile; derivatives thereof; and so forth.

As stated, the aromatic primary amine is generally capable of reacting with nitrite ions ("nitrites") under certain conditions. For instance, under acidic conditions, the nitrite ions form nitrous acid (nitric (III) acid), which has the formula $HNO_2$. Nitrous acid subsequently reacts with the aromatic primary amine to produce a diazonium ion. For instance, sulfanilamide ("SAA") can react with nitrous acid to form a diazonium ion as follows:

The resulting diazonium ion is an intermediate that is subsequently able to react with a detection reagent. Typically, the detection reagent is a nucleophilic (i.e., electron-rich) aromatic compound, such as a nucleophilic aromatic amine. Examples of such nucleophilic aromatic amines include, for instance, 8-hydroxyjulolidine, N,N-dimethylaniline; methylenedianiline; benzidine; benzoquinoline; aminoquinoline; m-phenylenediamine; α-trifluoro-m-toluidene; ortho-toluidine; m-aminophenol; ortho-tolidine; derivatives thereof; and so forth. One particularly suitable nucleophilic aromatic amine is N-1-naphthylethylene diamine ("NED"), which has the following structure:

In some cases, it can be desirable to select the detection reagent based on its ability to be readily immobilized onto a layer of the multi-layered device of the present disclosure. In this regard, the present inventor has discovered that certain macromolecular reagents (e.g., polymers, oligomers, dendrimers, particles, etc.) can be particularly useful in the present disclosure. Generally speaking, such macromolecular reagents contain at least two functionalities, i.e., a reactive moiety and a macromolecular moiety, which are covalently or noncovalently joined. A macromolecular moiety can include, for instance, a polymeric moiety, such as a linear or branched, homopolymer or copolymer. The polymeric moieties can be natural, synthetic, or combinations thereof. Examples of natural polymeric moieties include, for instance, peptides, proteins, DNA/RNA and polysaccharides (e.g., glucose-based polymers). Examples of synthetic polymeric moieties include, instance, polyacrylic acid and polyvinyl alcohols. One particular example of a suitable polysaccharide detection reagent is activated dextran (polymeric moiety) conjugated to N-1-naphthylethylene diamine (aromatic amine moiety).

As indicated, the macromolecular moiety can also be a particle. The particle can generally be joined to a reactive moiety using any of a variety of well-known techniques. For instance, covalent attachment of a particle to a substrate can be accomplished using carboxylic, amino, aldehyde, bromoacetyl, iodoacetyl, thiol, epoxy or other reactive functional groups, as well as residual free radicals and radical cations, through which a coupling reaction can be accomplished. A surface functional group can also be incorporated as a functionalized co-monomer because the surface of the particle can contain a relatively high surface concentration of polar groups. In certain cases, the particle can be capable of direct covalent bonding to a substrate without the need for further modification. It should also be understood that, besides covalent bonding, other attachment techniques, such as physical adsorption, can also be utilized in the present disclosure.

One particular technique for covalently bonding an aromatic amine reactive moiety to a particle will now be described in more detail. In this particular embodiment, the aromatic amine moiety is formed from N-(1-naphthyl)ethylenediamine ("NED"). The particle can be carboxylated latex particles available from Molecular Probes, Inc. or Bangs Laboratories, Inc. To covalently conjugate the particle with the aromatic amine, the carboxylic groups on the particle surface are first activated with a carbodiimide (e.g., ethylcarbodiimide hydrochloride (EDC)). Because NED possesses a primary amine group ($NH_2$), the activated carboxylic acid groups can then be reacted with the primary amine (—$NH_2$) group of NED to form an amide bond. This reaction can occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting detection reagent can then be blocked with ethanolamine, for instance, to block any remaining activated sites.

Regardless of the particular detection reagent selected, the intermediate compound formed by the initial nitrite reaction can subsequently react with the detection reagent to form an indicator having a different color. For example, a diazonium ion formed in the reaction between a nitrite and aromatic primary amine can electrophilically attack the nucleophilic or "electron-rich" ring system of a nucleophilic aromatic amine detection reagent. In one embodiment, for example, a N-1-naphthylethylene diamine detection reagent reacts with a diazonium ion to form an azo indicator according to the following reaction:

The absorption shift provides a color difference that is detectable, either visually or through instrumentation, to indicate the presence of nitrites within the test sample. For example, prior to contact with an infected test sample, the detection reagent can be colorless or it can possess a certain color. However, after reacting with the intermediate diazonium ion formed by the nitrite reaction described above, an aromatic azo indicator will form that exhibits a color that is different than the initial color of the detection reagent. As a result of the color change, the presence of nitrites in the test sample can be readily detected.

One particular embodiment of a method for detecting the presence of nitrites within a test sample using the device 10 of FIG. 1 will now be described in more detail. Initially, a test sample containing nitrites is applied to the device 10 and travels in the direction "D". The nitrites are able to mix and react with the aromatic primary amines at the sensing layer 12. The nitrites and aromatic primary amines react further to form intermediate diazonium ions. The diazonium ions then react with a nucleophilic aromatic amine detection reagent to form a colored azo indicator. After the reaction, the sensing layer 12 changes color, which can be indicative of urinary tract infection. The device 10 also includes a control layer 14 in fluid communication with the sensing layer 12. The test sample moves from the sensing layer 12 to the control layer 14 and thereby causes diffusive movement of a control reagent back to the sensing layer 12. The control reagent is capable of inhibiting the reaction at the sensing layer. Affecting the speed of the reaction can allow the sensing layer 12 to be tolerant of multiple urine insults without affecting the signal over an extended period of time.

Of course, the present disclosure is by no means limited to the diagnosis of urinary tract infection. Numerous health conditions can be diagnosed through testing of bodily fluids such as urine. Testing for even a single condition can require that multiple different analytes be targeted.

Still other analytes of interest can include proteins, enzymes, nitrites, ketones, various bacteria, red or white blood cells, glucose, bilirubin, urobilinogen, and so forth.

Figure 2:
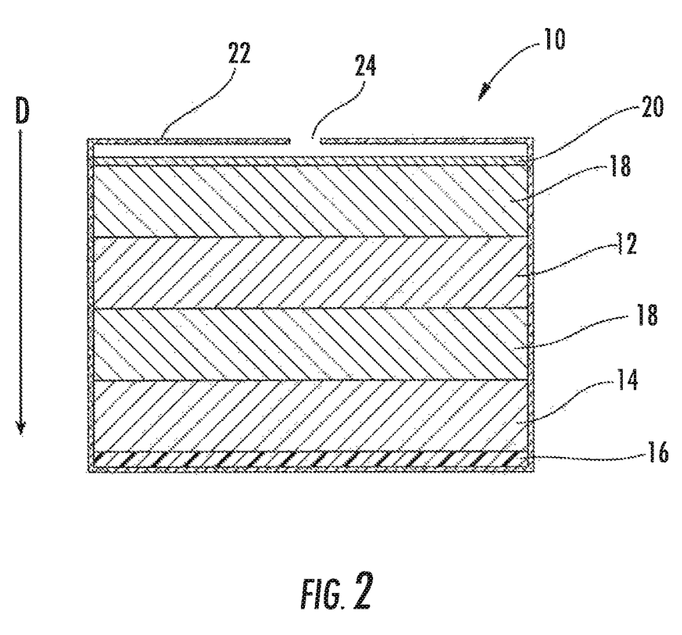
FIG. 2 is a perspective view of one embodiment of a device that can be used in the present disclosure.

In addition, with reference to FIG. 2, additional layer(s) 18 can be positioned between the sensing layer 12 and the control layer 14 to alter the diffusion rate and speed of the control reagents traveling to the sensing layer 12.

In this regard, one or more additional layer(s) can be included in the multi-layer device of the present disclosure. Such layers can serve as variety of purposes. However, such additional layer(s) are configured so as to not interfere with detection of the signal in the sensing layer(s). For instance, such layers can be of varying diameter, length, or shape so as to not cover the sensing layer(s) completely, yet still be vertically adjacent to the other layers of the device.

Referring again to FIG. 2, the additional layer(s) 18 can serve as a quenching layer. The quenching layer is configured to remove compounds from the test sample that would otherwise interfere with the accuracy of the detection system. For example, contaminants within the test sample (e.g., phenolics, bilirubin, urobilinogen, etc.) can react with the diazonium ion within the sensing layer 12 and form an aromatic azo compound, thereby producing a "false negative" result. Thus, the quenching layer can contain a quenching agent, such as a diazonium ion, that is capable of reacting with the reaction contaminants. It should be understood, however, that such a quenching agent can be applied directly to the sensing layer 12 rather than on a separate quenching layer. The quenching agent can be the same or different than the detection agent used within the sensing layer 12. Typically, the quenching agent is non-diffusively immobilized within the quenching layer in the manner described above so that it does not flow through to the sensing layer 12 and interfere with testing. The location of the quenching layer can vary, but is typically positioned upstream from the sensing layer 12 and the location at which the substrate is applied to avoid interference with analyte detection.

The one or more of the layers according to the present disclosure can be made from a porous membrane or can be formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, MgSO$_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, one or more of the layers can be formed from a glass fiber pad.

The size and shape of each layer can generally vary as is readily recognized by those skilled in the art. For instance, a layer can have a length of from about 10 to about 100 millimeters, in some embodiments from about 20 to about 80 millimeters, and in some embodiments, from about 40 to about 60 millimeters. The width of each layer can also range from about 0.5 to about 20 millimeters, in some embodiments from about 1 to about 15 millimeters, and in some embodiments, from about 2 to about 10 millimeters.

The layers of the present disclosure can be joined together so as to be in a vertically adjacent relationship. For example, referring to FIG. 1, the control layer is positioned directly underneath the sensing layer. In this manner, the layers can be in fluid communication with one another.

However, it should be understood that other suitable arrangements of the layers are also contemplated by the present disclosure. By way of example only, the control layer may not be positioned directly underneath the sensing layer, but rather, additional layers as further described herein can be present. In addition, certain layers can be in a horizontally adjacent relationship with one another. For example, multiple control layers can be present that are horizontally adjacent to one another but vertically adjacent to the sensing layer.

In addition, the various layers contemplated by the present disclosure can be assembled together as would be known to one of ordinary skill in the art. For example, in certain embodiments, the layers can be taped together or mechanically compressed together. In other embodiments, however, an adhesive can be utilized to keep the layers together. Any suitable adhesive as would be known to one of ordinary skill in the art can be utilized.

As stated above, in some embodiments, a support 16 carries one or more layers. For example, the support 16 can be positioned directly adjacent to one or more of the layers as shown in FIG. 1, or one or more intervening layers. Regardless, the support 16 can generally be formed from any material able to carry the layers. The support 16 can be formed from a material that is transmissive to light, such as transparent or optically diffuse (e.g., translucent) materials. Also, it is generally desired that the support 16 is liquid-impermeable so that fluid flowing through the layers does not leak through the support 16. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for a layer in accordance with the present disclosure, the support 16 is generally selected to have a certain minimum thickness. Likewise, the thickness of the support 16 is typically not so large as to adversely affect its optical properties. Thus, for example, the support 16 can have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers can be obtained from Millipore Corp. of Bedford, Mass. under the name "SHF180UB25."

As is well known the art, a layer can be cast onto the support 16, wherein the resulting laminate can be die-cut to the desired size and shape. Alternatively, a layer can simply be laminated to the support 16 with, for example, an adhesive.

The device 10 can also include one or more layers that control the diffusion rate of the test sample and/or reagents. For instance, such layer(s) can be configured from materials as described herein so as to slow the speed of the test sample and/or reagents as they flow through the device.

The device 10 can also contain an absorbent material 20 that is positioned adjacent to the one or more of the layers of the multi-layered device. For instance, in certain embodiments, the absorbent material 20 can serve as an application region for a test sample. Some suitable absorbent materials that can be used in the present disclosure include, but are not limited to, nitrocellulose, cellulosic materials, porous polyethylene pads, glass fiber filter paper, and so forth. The absorbent material can be wet or dry prior to being incorporated into the device 10. Pre-wetting can facilitate capillary flow for some fluids, but is not typically required. Also, as is well known in the art, the absorbent material can be treated with a surfactant to assist the wicking process.

Additionally, referring to FIG. 1, in certain embodiments one or more layers of the multi-layered device can be covered by a material. Such a cover material 22 that covers the layer(s) can define an opening 24 for the test sample. The opening 24 can be of sufficient size and dimension as would be known in the art to permit a test sample to contact the multi-layer device of the present disclosure. In certain embodiments, tape can be utilized as the cover material. Such a material can be utilized to hold the layers of the multi-layered device together. Additionally, such a material can prevent reagent from leaking out of the device.

The present disclosure provides a relatively simple, compact and cost-efficient device for accurately detecting the presence of analytes within a test sample (e.g., urine). The test result can be visible so that it is readily observed by the person performing the test for an extended period of time.

In accordance with the present disclosure, one or more devices can be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 3:
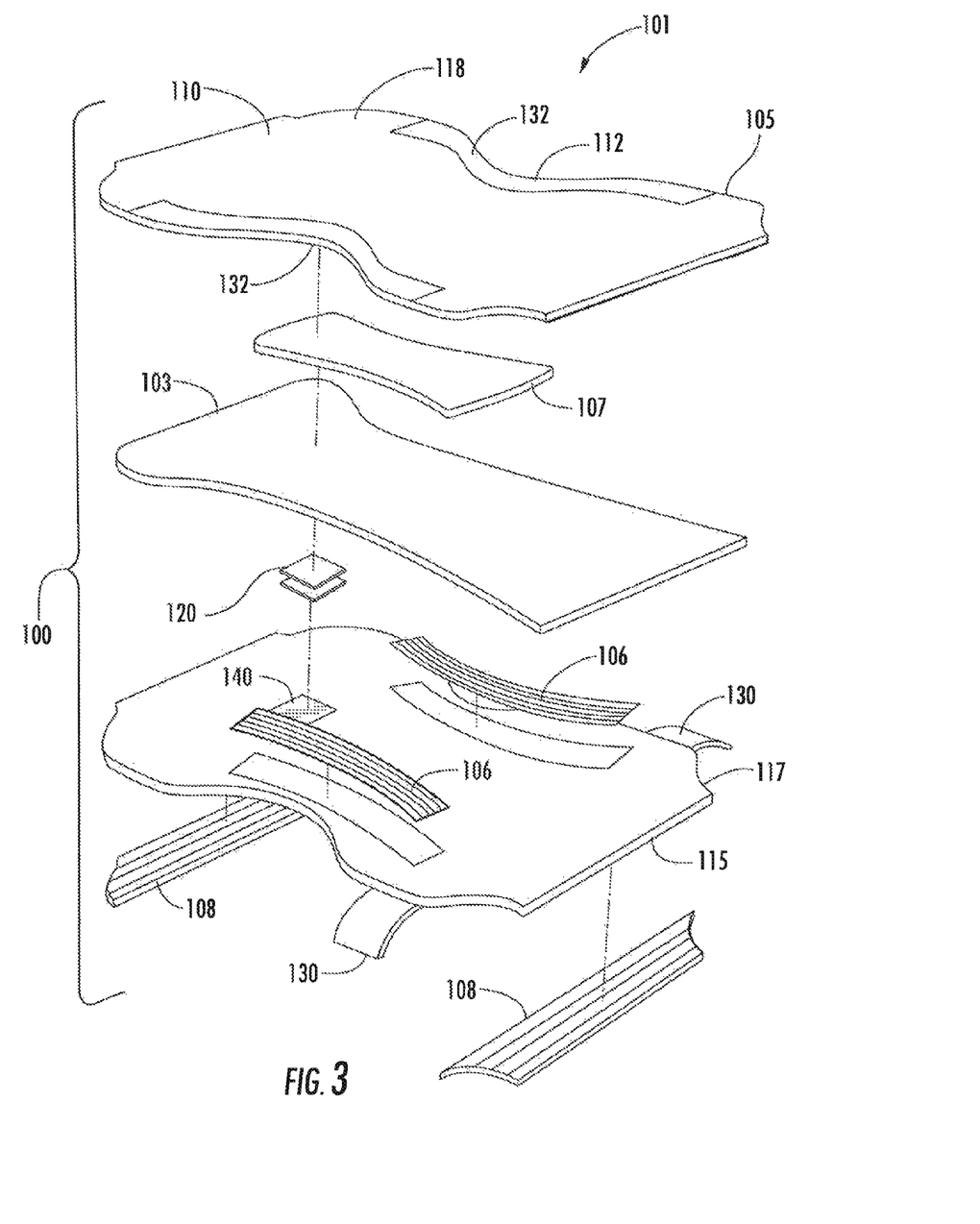
FIG. 3 is a perspective view of one embodiment of a device that can be used in the present disclosure.

Various embodiments of an absorbent article that can be formed according to the present disclosure will now be described in more detail. For purposes of illustration only, an absorbent article is shown in FIG. 3 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present disclosure. Likewise, one or more of the layers referred to in FIG. 3 can also be eliminated in certain exemplary embodiments of the present disclosure.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, I V. et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Ellis et al. and U.S. Pat. No. 5,490,846 to Ellis et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown) that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 3, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 3, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer.

The diaper 101 can also include one or more fasteners 130. For example, two flexible fasteners 130 are illustrated in FIG. 3 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

Generally speaking, the multi-layer devices of the present disclosure can be incorporated into the absorbent article in a variety of different orientations and configurations, so long as the device is capable of receiving the bodily fluid and providing a signal to a user or caregiver of the presence or absence of the analyte. For example, the sensing layer and/or control layer can be visible to the user or caregiver so that a simple, accurate, and rapid indication of the presence of the analyte can be provided. The visibility of such layer(s) can be accomplished in a variety of ways. For example, in some embodiments, the absorbent article can include a transparent or translucent portion 140 (e.g., window, film, etc.) that allows the detection zone and/or control zone to be readily viewed without removal of the absorbent article from the wearer and/or without disassembly of the absorbent article. In other embodiments, the detection zone and/or control zone can extend through a hole or aperture in the absorbent article for observation. In still other embodiments, the detection zone and/or control zone can simply be positioned on a surface of the absorbent article for observation.

Regardless of the particular manner in which it is integrated, a fluid such as urine can be directly discharged to a portion of the sensing layer, a liquid permeable cover or other material surrounding assay device 120, or can be discharged onto a component of the absorbent article into which the assay device 120 has been integrated.

After a sufficient reaction time, the intensity of the color at the sensing layer can be measured to quantitatively or semi-quantitatively determine the level of analyte present in the test sample. Nevertheless, while quantitative testing can be performed, qualitative testing is typically employed to provide early testing and monitoring of a health condition. Thus, when one or more analytes of interest are visually detected, the user or caregiver is given an indication that further quantitative testing can be undertaken. For example, a diaper having an integrated assay device can be periodically used with infants or non-ambulatory patients as part of a monitoring program that tests for UTI. Upon indication of a positive test result, further quantitative testing can then be undertaken to determine the scope and stage of the problem detected so a to provide additional treatment information.

The present disclosure can be better understood with reference to the following examples.

EXAMPLES

The ability to provide stable tests in accordance with the present disclosure was demonstrated.

Preparation of two-layered pads for nitrite detection: A glass fiber pad (Millipore Co.) was soaked with 1M sodium bicarbonate in water and was dried at 50° C. for 1 hour. The backing card from the pad was cut into 6 mm wide strips and a portion of the cover of the strip was peeled off. The pad with sodium bicarbonate was laid on the peeled area of the strip. A nitrite detecting pad from a urine analysis dipstick (Roche Diagnostics) was peeled off and laid on the top of the pad with sodium bicarbonate. A piece of tape (Scotch®, 3M Company) was punched to create a hole in the middle and used to secure the two pads together with the hole located in the middle of the pad.

Detecting nitrite in urine using the devices: 20 µl of nitrite-free urine was added to a first device and 20 µl of nitrite-containing urine (10 µg/ml) was added to the second device. No color was developed for the first device within 1 minute and a distinguishing pink color was developed for the second device. 20 µl of nitrite-free urine was added a urine analysis dipstick (Roche Diagnostics) and 20 µl of nitrite-containing urine was added a urine analysis dipstick (Roche Diagnostics). No color was observed on the first dipstick and pink color was observed on the second dipstick. Four hours later, strong pink color was observed for both dipsticks. However, no significant change was observed for the multi-layered devices. Apparently, the signal was stable for a longer period of time on the multi-layered devices when compared to the false positive that resulted on the urine analysis dipstick after an extended period of time.

While the disclosure has been described in detail with respect to the specific embodiments thereof, it will be appreciated that those skilled in the art, upon attaining an understanding of the foregoing, can readily conceive of alterations to, variations of, and equivalents to these embodiments. Accordingly, the scope of the present disclosure should be assessed as that of the appended claims and any equivalents thereto.

What is claimed is:

1. A multi-layered device for detecting the presence or absence of an enzyme within a test sample, the device comprising:
    a sensing layer, the sensing layer comprising a substrate capable of being modified in the presence of the enzyme to release a product utilized to indicate the presence or absence of the enzyme in the test sample; wherein the sensing layer is covered by a material defining an opening, the opening permitting the test sample to contact the sensing layer; and
    a control layer, the control layer being in fluid communication with and vertically adjacent to the sensing layer, the control layer including a control reagent capable of inhibiting the reaction at the sensing layer by diffusive movement of the control reagent from the control layer to the sensing layer.

2. The multi-layered device of claim 1, wherein the enzyme is an esterase.

3. The multi-layered device of claim 1, wherein the substrate is an aromatic ester.

4. The multi-layered device of claim 1, wherein the product comprises a nucleophilic aromatic compound.

5. The multi-layered device of claim 4, wherein the nucleophilic aromatic compound comprises benzopyrrole.

6. The multi-layered device of claim 1, wherein the sensing layer further comprises a diazonium ion.

7. The multi-layered device of claim 1, wherein the control layer is positioned underneath the sensing layer.

8. The multi-layered device of claim 1, wherein the control reagent comprises an enzyme inhibitor.

9. A multi-layered device for detecting the presence or absence of a nitrite within a test sample, the device comprising:
- a sensing layer, the sensing layer comprising an aromatic primary amine and a detection reagent, the aromatic primary amine capable of reacting with a nitrite to form a diazonium ion, the detection reagent capable of reacting with the diazonium ion to form an indicator, the indicator exhibiting a color indicative of the presence or absence of the nitrite in the test sample; wherein the sensing layer is covered by a material defining an opening, the opening permitting the test sample to contact the sensing layer; and
- a control layer, the control layer being in fluid communication with and vertically adjacent to the sensing layer, the control layer including a control reagent capable of inhibiting the reaction at the sensing layer by diffusive movement of the control reagent from the control layer to the sensing layer.

10. The multi-layered device of claim 9, wherein the aromatic primary amine comprises aniline; 4-chloroaniline; 4-bromoaniline; 2,4,6-tribromoaniline; 2,4,6-trichioroaniline; α-trifluoro-m-toluidene; ortho-toluidine; m- and p-aminophenol; ortho-tolidine; sulfanilamide, p-aminobenzoic acid; 1-amino-8-hydroxynaphthalene-3, 6-disulphonic acid; aminoacetoanilide; aminophenyl ether, p-arsalinic acid; 4-amino-1-naphthalenecarbonitrile, or derivatives thereof.

11. The multi-layered device of claim 9, wherein the detection reagent comprises a nucleophilic aromatic amine.

12. The multi-layered device of claim 9, wherein the indicator is an aromatic azo compound.

13. The multi-layered device of claim 9, wherein the control layer is positioned underneath the sensing layer.

14. The multi-layered device of claim 9, wherein the control reagent comprises a buffer, a base, or combinations thereof.

15. An absorbent article for receiving a bodily fluid suspected of containing an analyte, comprising:
- a substantially liquid impermeable layer;
- a liquid permeable layer;
- an absorbent core positioned between the substantially liquid impermeable layer and the liquid permeable layer; and
- a multi-layered device integrated into the article and positioned such that the device is in fluid communication with the bodily fluid when provided by a wearer of the article, the device comprising a sensing layer and a control layer, the sensing layer configured to support a reaction so as to exhibit a signal indicative of the presence or absence of the analyte in the bodily fluid, wherein the sensing layer is covered by a material defining an opening, the opening permitting the bodily fluid to contact the sensing layer; the control layer being in fluid communication with and vertically adjacent to the sensing layer, the control layer including a reagent capable of inhibiting the reaction at the sensing layer by diffusive movement of the reagent from the control layer to the sensing layer.

16. The absorbent article of claim 15, wherein the absorbent article defines a window through which the sensing layer, the control layer, or both are observable.

17. The absorbent article of claim 15, wherein the control layer is positioned underneath the sensing layer.

* * * * *